(12) United States Patent
Keyser et al.

(10) Patent No.: US 12,115,138 B2
(45) Date of Patent: Oct. 15, 2024

(54) TETRAHYDROCURCUMIN COMPOSITIONS, METHODS OF MAKING, AND METHODS OF USING THE SAME

(71) Applicant: RENIBUS THERAPEUTICS, INC., Southlake, TX (US)

(72) Inventors: Donald Jeffrey Keyser, Southlake, TX (US); Alvaro F. Guillem, Lantana, TX (US); Bhupinder Singh, Phoenix, AZ (US); Richard A. Zager, Mercer Island, WA (US)

(73) Assignee: RENIBUS THERAPEUTICS, INC., Southlake, TX (US)

( * ) Notice: Subject to any disclaimer, the term of this patent is extended or adjusted under 35 U.S.C. 154(b) by 0 days.

(21) Appl. No.: 16/811,759

(22) Filed: Mar. 6, 2020

(65) Prior Publication Data

US 2020/0281871 A1  Sep. 10, 2020
US 2021/0308074 A9  Oct. 7, 2021

Related U.S. Application Data

(60) Provisional application No. 62/955,577, filed on Dec. 31, 2019, provisional application No. 62/814,426, filed on Mar. 6, 2019.

(51) Int. Cl.
*A61K 31/12* (2006.01)
*A61K 9/127* (2006.01)
(Continued)

(52) U.S. Cl.
CPC .............. *A61K 31/12* (2013.01); *A61K 9/127* (2013.01); *A61K 31/145* (2013.01); *A61K 31/16* (2013.01);
(Continued)

(58) Field of Classification Search
CPC ........ A61K 31/12; A61K 9/127; A61K 47/24; A61K 31/355; A61K 31/375; A61K 47/34;
(Continued)

(56) References Cited

U.S. PATENT DOCUMENTS 9,375,408 B2 *  6/2016  Singh ................... A61K 31/145
2005/0209187 A1  9/2005  Newton et al.
(Continued)

FOREIGN PATENT DOCUMENTS

CN  104739751 A  7/2015
DE    862482 C  1/1953
(Continued)

OTHER PUBLICATIONS

Murugan, P., et al in Basic & Clinical Pharmacology & Toxicology, vol. 99, pp. 122-127, 2006.*

(Continued)

*Primary Examiner* — Gollamudi S Kishore
(74) *Attorney, Agent, or Firm* — Jeff B. Vockrodt; Culhane PLLC (57) ABSTRACT

The present invention relates to novel tetrahydrocurcumin (THCu) compositions, novel methods of manufacturing, and methods of using these compositions for therapeutic applications. The novel synthetic pathway(s) result in THCu compositions that generally lack hexahydrocurcumin (HHC), and include an improved impurity profile with reduced additional species that are generally present in hydrogenated curcumin compositions.

17 Claims, 9 Drawing Sheets

(51) Int. Cl.

| | |
|---|---|
| *A61K 31/145* | (2006.01) |
| *A61K 31/16* | (2006.01) |
| *A61K 31/355* | (2006.01) |
| *A61K 31/375* | (2006.01) |
| *A61K 31/385* | (2006.01) |
| *A61K 31/7048* | (2006.01) |
| *A61K 47/10* | (2017.01) |
| *A61K 47/24* | (2006.01) |
| *A61K 47/34* | (2017.01) |

(52) U.S. Cl.
CPC .......... *A61K 31/355* (2013.01); *A61K 31/375* (2013.01); *A61K 31/385* (2013.01); *A61K 31/7048* (2013.01); *A61K 47/10* (2013.01); *A61K 47/24* (2013.01); *A61K 47/34* (2013.01)

(58) Field of Classification Search
CPC .. A61K 31/145; A61K 31/16; A61K 31/7048; A61K 47/10; A61K 31/385; A61K 9/0019
See application file for complete search history.

(56) References Cited

U.S. PATENT DOCUMENTS

| | | |
|---|---|---|
| 2013/0225689 A1 | 8/2013 | Khamar et al. |
| 2016/0058713 A1 | 3/2016 | Singh |
| 2018/0333388 A1 | 11/2018 | Ling |
| 2020/0281871 A1 | 9/2020 | Keyser et al. |

FOREIGN PATENT DOCUMENTS

| | | |
|---|---|---|
| DE | 19547356 A1 | 6/1997 |
| JP | H11246398 | * 12/2015 |
| WO | 2011/047309 | * 4/2011 |
| WO | 2018148217 A1 | 8/2018 |
| WO | 2019019091 A1 | 1/2019 |

OTHER PUBLICATIONS

Setthacheewakul, S., et al in AAPS Pharm Sci Tech, vol. 12, # 1, pp. 152-164.*

Notification of Transmittal of the International Search Report and the Written Opinion of the International Searching Authority received in Application No. PCT/US2020/020517 dated Jun. 18, 2020, 14 pages.

International Search Report received in Application No. PCT/US20/67670 dated Mar. 29, 2021, 3 pages.

Pan, et al., "Biotransformation of Curcumin Through Reduction and Glucuronidation in Mice," Drug Metabolism and disposition, vol. 27, No. 1, The American Society for Pharmacology and Experimental Therapeutics, Received Mar. 17, 1998; accepted Dec. 10, 1998, 57 pages.

Ravikumar, et al., "A Toxicological Evaluation of a Standardized Hydrogenated Extract of Curcumin (Curo White)," Hindawi, Journal of Toxicology, vol. 2018, Article ID 5243617, Jan. 23, 2018, 17 pages.

Written Opinion received in Application No. PCT/US20/67670 dated Mar. 29, 2021, 5 pages.

Written Opinion received in International Application No. PCT/US20/21552 dated May 11, 2020, 6 pages.

* cited by examiner

Appendix II
Descriptive Statistics for Plasma Concentrations

| Test Article | Group | Dose (pg/kg) | Scheduled Time (hr) | N | Arithmetic Mean | Standard Error | CV (%) | Geometric Mean | CV (%) | Minimum | Median | Maximum |
|---|---|---|---|---|---|---|---|---|---|---|---|---|
| THCu | 1 | 1000 | 0 | 3 | 0.00 | 0.00 | . | . | . | 0.00 | 0.00 | 0.00 |
| | | | 1 | 3 | 5,126.09 | 2,548.36 | 86.11 | 4,069.04 | 95.30 | 2,312.53 | 2,852.49 | 10,213.26 |
| | | | 2 | 3 | 2,350.17 | 243.44 | 17.94 | 2,326.30 | 17.40 | 2,050.15 | 2,160.10 | 2,832.26 |
| | | | 4 | 3 | 1,832.12 | 171.60 | 16.22 | 1,816.92 | 15.69 | 1,647.57 | 1,673.80 | 2,174.99 |
| | | | 8 | 3 | 1,363.59 | 160.04 | 20.33 | 1,343.92 | 21.40 | 1,066.39 | 1,409.29 | 1,615.10 |
| | | | 12 | 3 | 1,430.60 | 306.23 | 37.08 | 1,360.73 | 41.23 | 889.94 | 1,451.74 | 1,950.12 |
| | | | 16 | 3 | 1,554.68 | 211.60 | 23.57 | 1,527.71 | 22.66 | 1,204.86 | 1,407.25 | 1,971.95 |
| | | | 24 | 3 | 1,211.90 | 330.13 | 47.18 | 1,111.76 | 56.69 | 626.02 | 1,241.17 | 1,768.50 |
| THCu-d6 | 2 | 1000 | 0 | 3 | 0.00 | 0.00 | . | . | . | 0.00 | 0.00 | 0.00 |
| | | | 1 | 3 | 2,288.01 | 654.03 | 49.51 | 2,125.38 | 48.01 | 1,692.79 | 1,635.07 | 3,596.16 |
| | | | 2 | 3 | 1,803.87 | 407.96 | 39.17 | 1,708.17 | 42.69 | 1,122.87 | 1,773.63 | 2,525.12 |
| | | | 4 | 2 | 2,584.80 | 1,487.61 | 81.39 | 2,113.81 | 116.75 | 1,097.19 | 2,584.80 | 4,072.42 |
| | | | 8 | 3 | 1,265.54 | 353.95 | 48.44 | 1,176.39 | 46.36 | 810.32 | 1,023.67 | 1,962.64 |
| | | | 12 | 3 | 1,400.31 | 228.22 | 28.23 | 1,365.27 | 27.74 | 1,084.07 | 1,273.40 | 1,843.47 |
| | | | 16 | 3 | 1,640.04 | 130.30 | 13.76 | 1,629.21 | 14.33 | 1,387.64 | 1,710.01 | 1,822.46 |
| | | | 24 | 3 | 2,902.92 | 557.09 | 33.24 | 2,804.63 | 32.35 | 2,189.73 | 2,518.18 | 4,000.84 |

Fig. 3

Appendix III
Individual Animal Pharmacokinetic Parameters

| Test Article | Group | Dose (mg/kg) | Animal Number | Cmax (ng/mL) | Tmax (hr) | AUC(0-t) (hr×ng/mL) | Final Time C>=LOQ |
|---|---|---|---|---|---|---|---|
| THCa | 1 | 1000 | 1001 | 10,213.26 | 1.0 | 54,153.22 | 24.0 |
|  |  |  | 1002 | 2,312.53 | 1.0 | 32,279.96 | 24.0 |
|  |  |  | 1003 | 2,852.49 | 1.0 | 32,067.48 | 24.0 |
| THCa-d6 | 2 | 1000 | 2001 | 4,072.42 | 4.0 | 54,545.49 | 24.0 |
|  |  |  | 2002 | 2,189.73 | 24.0 | 39,370.98 | 24.0 |
|  |  |  | 2003 | 2,518.18 | 24.0 | 37,108.13 | 24.0 |

TETRAHYDROCURCUMIN COMPOSITIONS, METHODS OF MAKING, AND METHODS OF USING THE SAME

BACKGROUND OF THE INVENTION

The present invention relates to novel tetrahydrocurcumin (THCu) compositions, novel methods of manufacturing, and methods of using these compositions for therapeutic applications.

THCu, as described herein, is a major metabolite of the curcuminoid, curcumin and can be used for its anti-fibrotic and anti-oxidant activities. THCu is a strong anti-oxidative molecule, and can be obtained by the hydrogenation of curcumin. THCu can be used as an anti-oxidant in oxidative stress diseases. Although THCu is relatively safe at high dosages (80 mgs/kg body weight), one of the major disadvantages of THCu is its low solubility, in which it has poor solubility in water at acidic and at physiological pH. Another disadvantage is its ability to hydrolyze rapidly in basic solutions.

U.S. Pat. No. 9,375,408 issued Jun. 28, 2016, to Dr. Bhupinder Singh describes the production of THCu through hydrogenation of curcumin. The '408 patent discloses that THCu is poorly absorbed and is rapidly metabolized. In order to increase the half-life of THCu, the '408 patent discloses the deuteration of THCu. Deuteration at one or two alcohol sites of THCu can delay glucuronidation, thus improving the half-life of THCu.

The inventors have discovered several problems with the hydrogenation of curcumin, and novel synthetic methods are needed for the production of THCu compositions.

SUMMARY OF THE INVENTION

The present invention involves a pharmaceutical formulation comprising tetrahydrocurcumin (THCu) and lacking detectable amounts of HHC. In one aspect, the invention involves a pharmaceutical formulation comprising a second component having a relative retention time between that of THCu and HHC. In another aspect, the THCu composition includes only one component with a retention time that is greater than that of THCu.

The present invention involves pharmaceutical formulations comprising the above THCu composition combined with a liposome carrier composition. In one aspect, the liposome carrier comprises a first lipid, wherein the first lipid is polyenylphosphatidylcholine. In one aspect, the composition comprises at least 5% of the polyenylphosphatidylcholine by weight and no more than 95% of the polyenylphosphatidylcholine by weight.

In another aspect, the formulation may further comprise an antioxidant selected from Vitamin E, Vitamin C or alpha lipoic acid. The composition in another aspect may comprise at least 5% of antioxidant by weight and no more than 95% of the antioxidant by weight. In another aspect, the composition may comprise an excipient, wherein the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). The composition may alternatively or, in addition, further comprise a lipophilic solvent, a fatty oil, or an organic oil.

The invention also relates to a method of treating or preventing a disorder, wherein the method comprises administering the pharmaceutical formulation of any of the foregoing claims to a patient in need thereof. In one aspect the disorder is selected from kidney disease, chronic kidney disease, and polycystic kidney disease.

DETAILED DESCRIPTION

Synthesis of THCu was achieved earlier by hydrogenation of curcumin, which has the following formula:

Curcumin can be hydrogenated resulting in a composition comprising THCu, which has the following structure:

There are several drawbacks to hydrogenation. Curcumin has limited solubility in non-polar solvents. When polar solvents are used for the hydrogenation, several undesirable (overreduced) reaction products are formed, such as hexahydrocurcumin and octahydrocurcumin. For large scale manufacturing hydrogenation in the last step is not a viable option, especially with curcumin which has a limited solubility. Hence an alternative route of synthesis is needed to synthesize THCu.

Example 1

Several routes were attempted for the synthesis of THCu (THCu), but were unsuccessful in making THCu. Here, we report only the route in which we were successful in making THCu. Ferulic acid (1) is abundantly available from plants and is a very cheap source of raw material. Reduction of ferulic acid followed by protection of the phenol with benzoate results in 3 in high yields. From the acid chloride of 3 we can make the β-ketoester 5, which on further alkylation with another molecule of the acid chloride results in 6. More experiments are needed to optimize the conversion of acid chloride to 6. Krapcho deethoxycarbonylation followed by the hydrolysis of benzoate results in THCu.

Ferulic acid (1) (20.0 g, 0.103 mol) was dissolved in a mixture of dichloromethane (150 mL) and methanol (70 mL). To this solution 5% Pd/C (1.0 g) was added and the mixture hydrogenated at 50 psi in Parr hydrogenator for 16 h. The reaction mixture was filtered through a plug of Celite and washed thoroughly with dichloromethane (50 mL). The volatiles were removed under vacuo to obtain 2 (20.2 g, quantitative) as white solid. 1H NMR (200 MHz, CDCl3) δ 2.62 (t, 2H), 2.9 (t, 2H), 3.85 (s, 3H), 6.72 (d, 1H), 6.74 (s, 1H), 6.82 (d, 1H).

Compound 2 (6.28 g, 32.0 mmol) was dissolved in 0.75 M aqueous sodium hydroxide solution (130 mL). Benzoyl chloride (4.1 mL, 35.2 mmol) was added to the above solution while keeping the solution cold. The reaction mixture was stirred for 16 h at room temperature. The reaction mixture was washed with ethyl acetate (50 mL). The aqueous layer was then acidified with 6 N HCl until the pH was 3. The aqueous layer was extracted with ethyl acetate (2×200 mL). The combined ethyl acetate layer was washed with water (50 mL) and brine (50 mL). The organic layer was then dried over Na2SO4, filtered, concentrated under reduced pressure. The tan solid was triturated with 20% ethyl acetate in hexanes to obtain off-white solid which was washed with the same solvent system. The solid was dried under high vacuum to give 3 (7.7 g, 80.2%). 1H NMR (200 MHz, CDCl3) δ 2.72 (t, 2H), 3.0 (t, 2H), 3.81 (s, 3H), 6.82 (d, 1H), 6.86 (s, 1H), 7.08 (d, 1H), 7.55 (t, 2H), 7.62 (t, 1H), 8.22 (d, 2H).

Compound 3 (17.8 g, 59.3 mmol) was suspended in a mixture of dichloromethane (200 mL) and N, N'-dimethylformamide (1.0 mL). To this suspension oxalyl chloride (14.8 mL, 177.9 mmol) was added over a period of 10 min. The reaction mixture was stirred at RT for 1 h, during which the solution becomes clear. The reaction mixture was concentrated in the rotary evaporator to obtain light yellow foamy solid, 4, which was used as is without any further purification and characterization.

Triethyl amine (10.5 mL, 75.0 mmol) was added to a suspension of potassium salt of ethyl malonate (5.1 g, 30.0 mmol) in acetonitrile (100 mL) and cooled to 0° C. To this suspension, anhydrous magnesium chloride (4.28 g, 45.0 mmol) was added and the mixture was continued to stir for another 1 h. Compound 4 (9.42 g, 30.0 mmol) was then added and the mixture allowed to stir at RT for 18 h. The reaction mixture was cooled to 0° C. and acidified to pH 2 with 6 N HCl. The crude product was extracted with ethyl acetate (2×200 mL). The combined ethyl acetate layer was washed with water (50 mL) and brine (50 mL). The organic layer was then dried over Na2SO4, filtered, concentrated under reduced pressure. Purification of the mixture using silica gel chromatography yielded 5 (3.8 g, 34.2%). This step needs to be optimized to get a better yield. 1H NMR (200 MHz, CDCl3) δ 1.28 (t, 3H), 2.95 (s, 4H), 3.42 (s, 2H), 3.80 (s, 3H), 4.20 (q, 2H), 6.80 (d, 1H), 6.83 (s, 1H), 7.05 (d, 1H), 7.55 (t, 2H), 7.62 (t, 1H), 8.22 (d, 2H).

To a solution of 5 (3.8 g, 10.3 mmol) in THF (40 mL) cooled to 0° C., sodium hydride (0.45 g, 60% in mineral oil) was added over a period of 10 min. The reaction mixture was stirred for 1 h at RT after which compound 4 (3.14 g, 10.3 mmol) was added and the mixture stirred at RT for 18 h. The reaction mixture was quenched with 10% NaHSO4 and extracted with ethyl acetate (2×100 mL). The combined ethyl acetate layer was washed with water (50 mL) and brine (50 mL). The organic layer was then dried over Na2SO4, filtered, concentrated under reduced pressure. Purification of the mixture with silica gel chromatography yielded 6 (1.2 g, 17.9%). This step needs to be optimized to get a better yield. 1H NMR (200 MHz, CDCl3) δ 1.30 (t, 3H), 3.0 (s, 8H), 3.80 (s, 6H), 4.24 (q, 2H), 6.80 (d, 2H), 6.83 (s, 2H), 7.05 (d, 2H), 7.55 (t, 4H), 7.62 (t, 2H), 8.20 (d, 4H), 17.75 (s, 1H).

The compound 6 (0.80 g, 1.23 mmol) was dissolved in DMSO (8 mL). To this solution solid sodium chloride (78 mg, 1.35 mmol) and water (1 drop) were added and the mixture stirred at 150° C. for 3 h. The reaction mixture was cooled to RT, quenched with water (20 mL) and extracted with EtOAc (2×20 mL). The combined ethyl acetate layer was washed with water (50 mL) and brine (50 mL). The organic layer was then dried over Na2SO4, filtered and concentrated under reduced pressure to obtain 7 (700 mg, quantitative) as white solid. Sodium metal (30 mg, 1.3 mmol) was stirred in methanol (10 mL) until all of sodium reacted. To this solution, compound 7 was added as methanol solution (3 mL). The reaction was stirred at RT for 3 h and the volatiles were evaporated under vacuo. The reaction mixture was quenched with 10% sodium bisulfate solution and extracted with ethyl acetate (2×20 mL). The combined ethyl acetate layer was washed with water (50 mL) and brine (50 mL). The organic layer was then dried over Na2SO4, filtered, concentrated under reduced pressure. Purification of the mixture with silica gel chromatography yielded THCu (0.44 g, quantitative). 1H NMR (200 MHz, CDCl3) δ 2.58 (m, 4H), 2.80 (m, 4H), 3.82 (s, 6H), 5.42 (s, 1H), 5.50 (d, 2H), 6.65 (m, 4H), 6.82 (d, 2H), 15.50 (s, 1H).

Example 2

The resulting composition from Example 1 was analyzed by gas chromatography, and compared to (A) a commercially available THCu prepared by hydrogenation of curcumin, (B) an in-house THCu product prepared by hydrogenation of curcumin, (C) hexahydrocurcumen (HHC), (D) a small scale synthesis of THCu according to the process of Example 1, and (E) a large scale synthesis of THCu according synthetic pathway described in Example 1.

TABLE I

| | | | | Gas Chromatography Analysis Relative Retention Time (RRT) | | | | |
|---|---|---|---|---|---|---|---|---|
| A | | | | 7.14 | 9.07 | | | 12.52 |
| B | | ~4.5 | ~6.5 | 7.14 | 9.07 | 9.93 | 10.86 | 13.75 |
| C (HHC) | | | | 7.15 | | | | |
| D | | | ~5.25 | | ~8.25 | 9.07 | 9.92 | |
| E | ~2.75 | | | | 8.23 | 9.07 | | |
| Species | | | | HHC | THCu | | | |

The synthetic pathway according to embodiments of the invention results composition comprising predominantly THCu and lacking detectable amounts of the over-hydrogenated impurity HHC.

Example 3

The composition of Example 1 is combined with liposomes to make a THCu pharmaceutical formulation. The liposome is polyenylphosphatidylcholine. The composition includes between 5% and 95% polyenylphosphatidylcholine.

Example 4

The composition of Example 3 is administered to a patient suffering from a disorder selected from kidney disease, chronic kidney disease, and polycystic kidney disease.

Example 5

Figure 1:
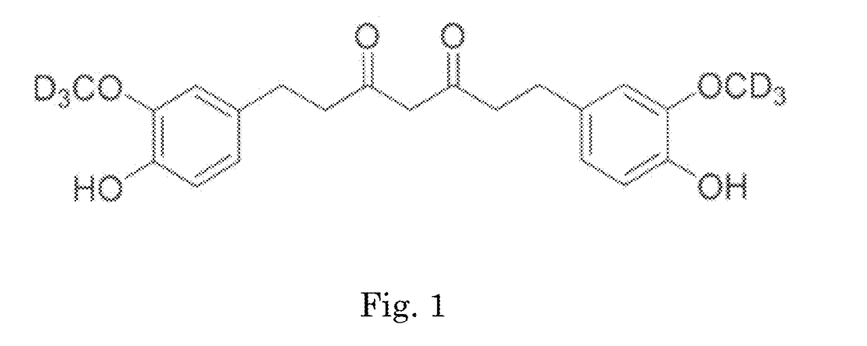
FIG. 1 shows d6-Tetrahydrocurumin according to an aspect of the invention.

In one aspect, the invention includes making a d6-Tetrahydrocurumin of the following formula:

The d6-THCu was formulated at a concentration of 10% w/w in the amounts and ratios provided below:

| Ingredient | Concentration % w/w | Amount/ Batch (g) |
|---|---|---|
| Tetrahydrocurcumin | 10.0 | 354.97[1] |
| Phosal ® 75 SA | 20.0 | 700.00 |
| Captex ® 300 | 5.0 | 175.0 |
| Labrasol ® ALF | 65.0 | 2275.0 |
| Total | 100.0 | 3504.97 |

The THCu weight was adjusted based on purity of API. Per CoA, purity is 98.6%. Phosal 75 ® SA is a phosphatidylcholine source for nutritional supplements, which includes lecithin in alcohol, safflower oil, glyceryl stearate, coconut oil, and ascorbyl palmitate that is sold by American Lecithin Company. Captex® 300 is also known as Medium Chain Triglycerides (MCT), and is sold by Abitec. The Captex composition includes 6.0% max of 6:0 Caproic Acid, 55.5-85.0% 8:0 Caprylic Acid, 15.0-40.0% 10:0 Capric Acid and 4.0% max 12:0 lauric acid. Labrasol® ALF (Caprylocaproyl Polyoxyl-8 glycerides) is a nonionic water-dispersible surfactant for lipid-based formulation to solubilize and increase oral bioavailability of poorly water-soluble APIs which is marketed by Gattefosse. Labrasol® ALF consists of a small fraction of mono-, di- and triglycerides and mainly PEG-8 (MW 400) mono- and diesters of caprylic ($C_8$) and capric ($C_{10}$) acids Labrasol® ALF self-emulsifies in aqueous media forming a fine dispersion, i.e., microemulsion (SMEDDS).

Compositions were prepared according to the following process. Set up the 5 L jacketed reaction vessel and Julabo circulation heater. Begin heating the Julabo to 90° C. Dispense Phosal 75 SA, Captex 300, and Labrasol ALF (Items 2, 3, and 4) into appropriately sized containers. Add the Phosal 75 SA, Captex 300, and Labrasol ALF to the 5 L reaction vessel. Mix contents until visually homogenous and product reaches a temperature of 85° C.±5° C. Add Tetrahydrocurcumin to vessel containing Phosal 75 SA, Captex 300, and Labrasol ALF while stirring. Mix until completely dissolved and visually homogenous. Reduce the Julabo temperature and allow the solution to cool to 30° C.±5° C. while continuing to stir. Package product by adding 50 mL to appropriate 60 mL bottles. Continue until product is exhausted.

The d6-THCu version of the compound provides a desirable release profile compared to non-deuterated THCu. Compositions were prepared using THCu as well as d6-THCu and their pk profiles were compared. As shown in FIG. 1, d6-THCu has a stabile release profile over time compared to THCu. FIG. 1 shows the geometric mean plasma concentrations of THCu and d6-THCu after oral administration of a single 100 mg dose of each test article to male rats—linear (left panel) and semi-logarithmic (right panel) axes.

The data from FIG. 1 is summarized in the following table comparing Cmax and Tmax of THCu-d6 and THCu:

|  | Test Article | |
| --- | --- | --- |
| Parameter* | THCu | THCu-d6 |
| Cmax (ng/mL) | 4069 [95.3](3) | 2,821 [33.4] (3) |
| Tmax (hr) | 1.0 (3) [1.0-1.0] | 24.0 (3) [4.0-24.0] |
| AUC(0–t)(hr × ng/mL) | 38,271 [30.8] (3) | 43,033 [21.0](3) |

*Geometric mean [geometric % CV] (N) except Tmax for which the median (N) [Range] are reported. Additional descriptive statistics can be found Fig. 4.

Figure 2:
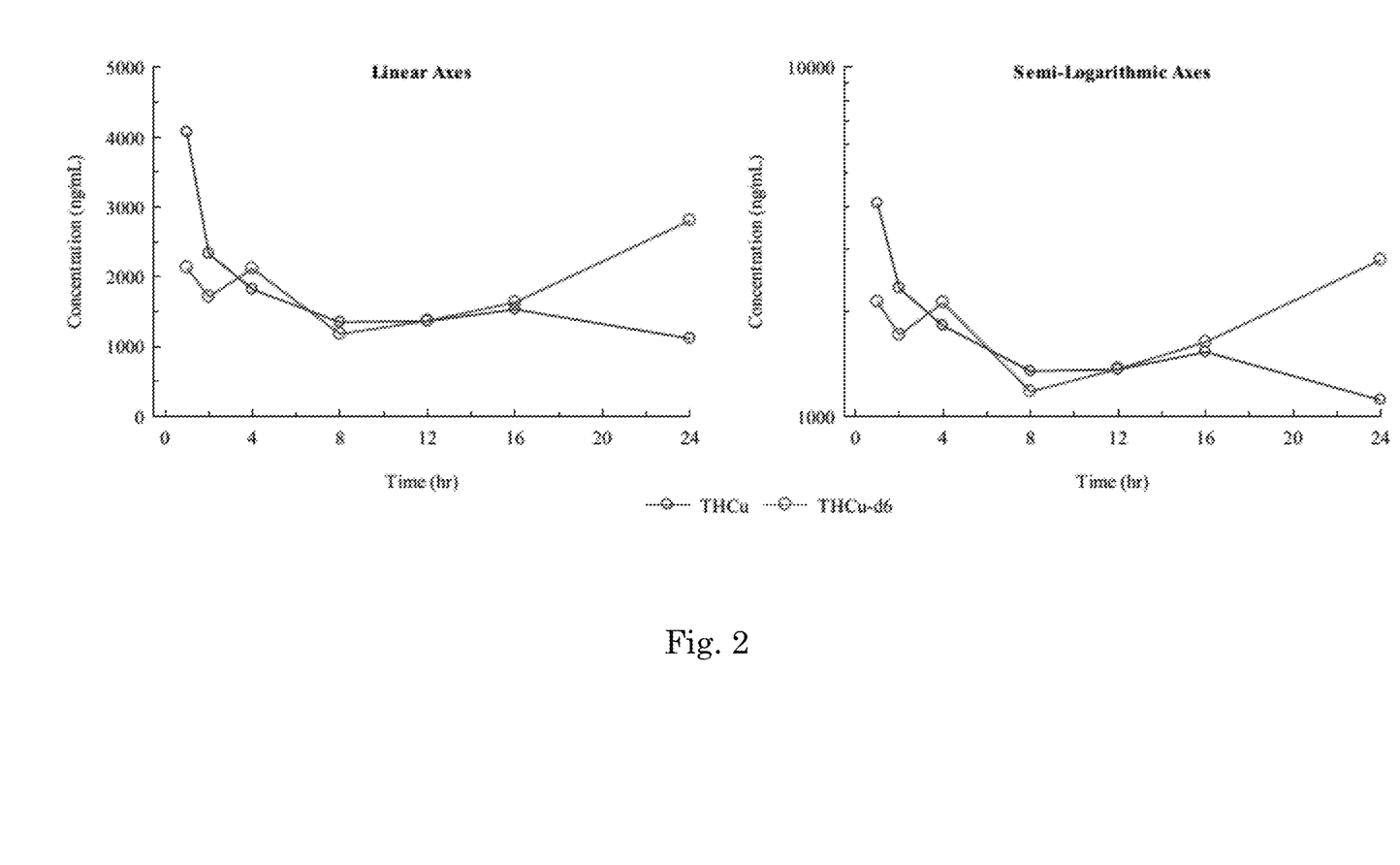
FIG. 2 shows the geometric mean plasma concentrations of THCu and d6-THCu after oral administration of a single 100 mg dose of each test article to male rats—linear (left panel) and semi-logarithmic (right panel) axes.
Figure 3:
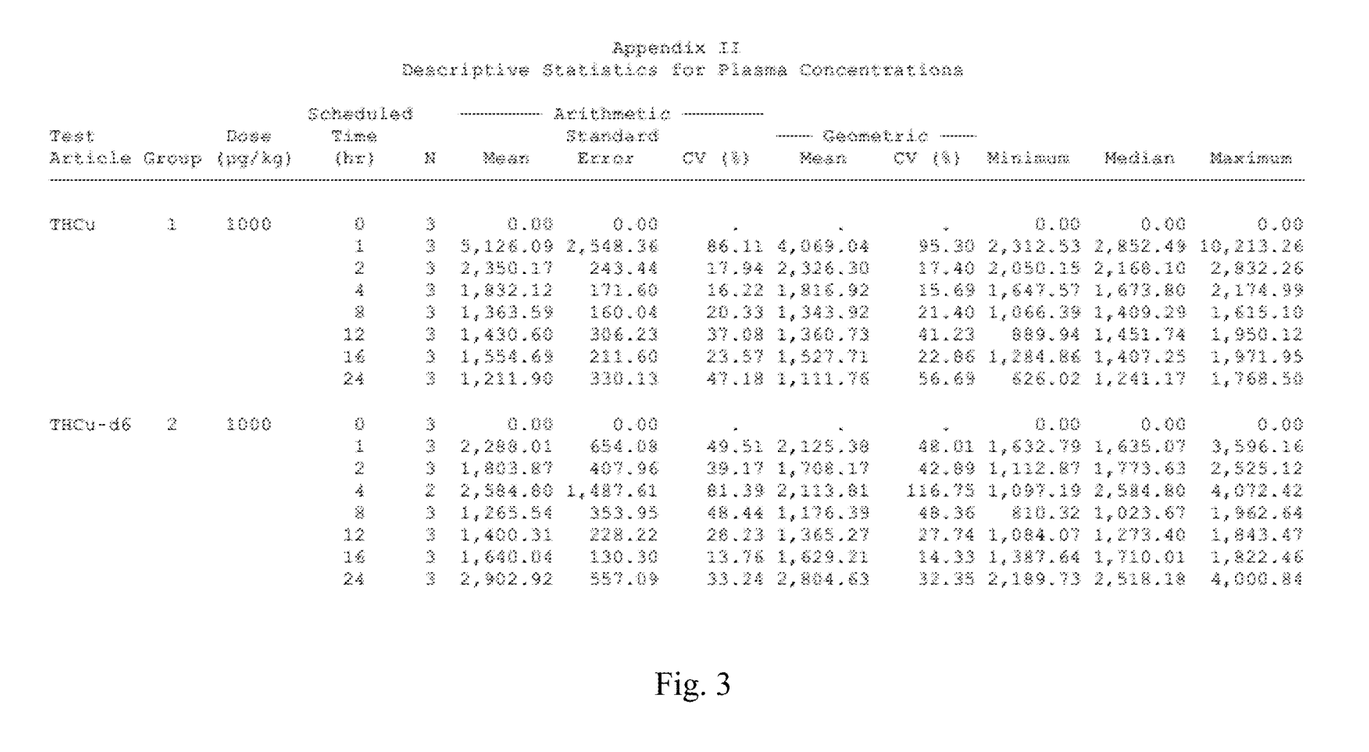
FIG. 3 shows descriptive statistics for plasma concentrations comparing THCu and d6-THCu.
Figure 4:
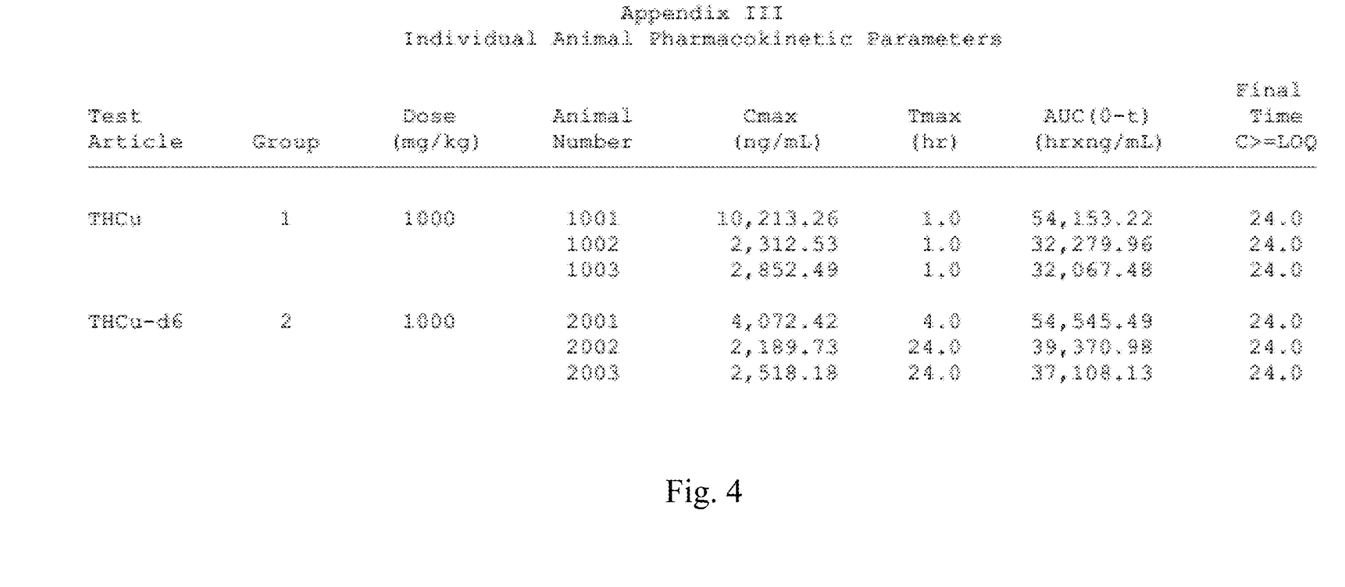
FIG. 4 shows individual animal pharmacokinetic parameters comparing THCu and d6-THCu.
Figure 5:
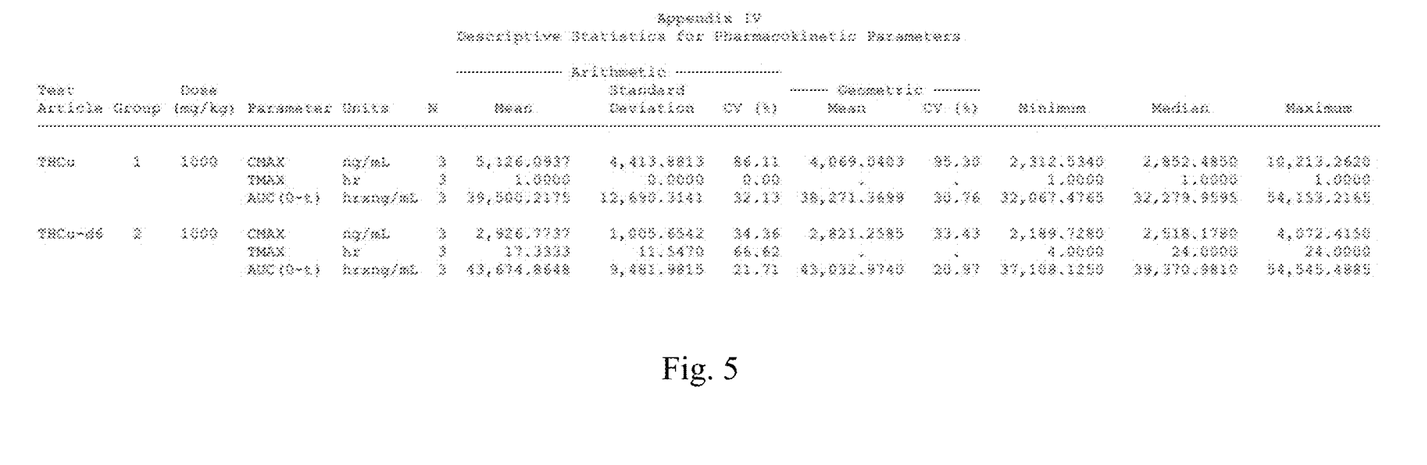
FIG. 5 shows descriptive statistics for pharmacokinetics parameters comparing THCu and d6-THCu.

The plasma concentrations of THCu and THCu-d6 was compared by administering single doses of 100 mg to male rats. FIG. 2 shows the geometric mean plasma concentrations of THCu and d6-THCu after oral administration of a single 100 mg dose of each test article to male rats—linear (left panel) and semi-logarithmic (right panel) axes. As shown in FIG. 2, the deuterated THCu-d6 had a more stable release profile than the non-deuterated version. The descriptive statistics for plasma concentration measurements comparing THCu and d6-THCu is shown in FIG. 3. Individual animal pharmacokinetic parameters comparing THCu and d6-THCu is shown in FIG. 4, and statistics for the individual animal pharmacokinetic parameters is shown in FIG. 5.

Figure 6:
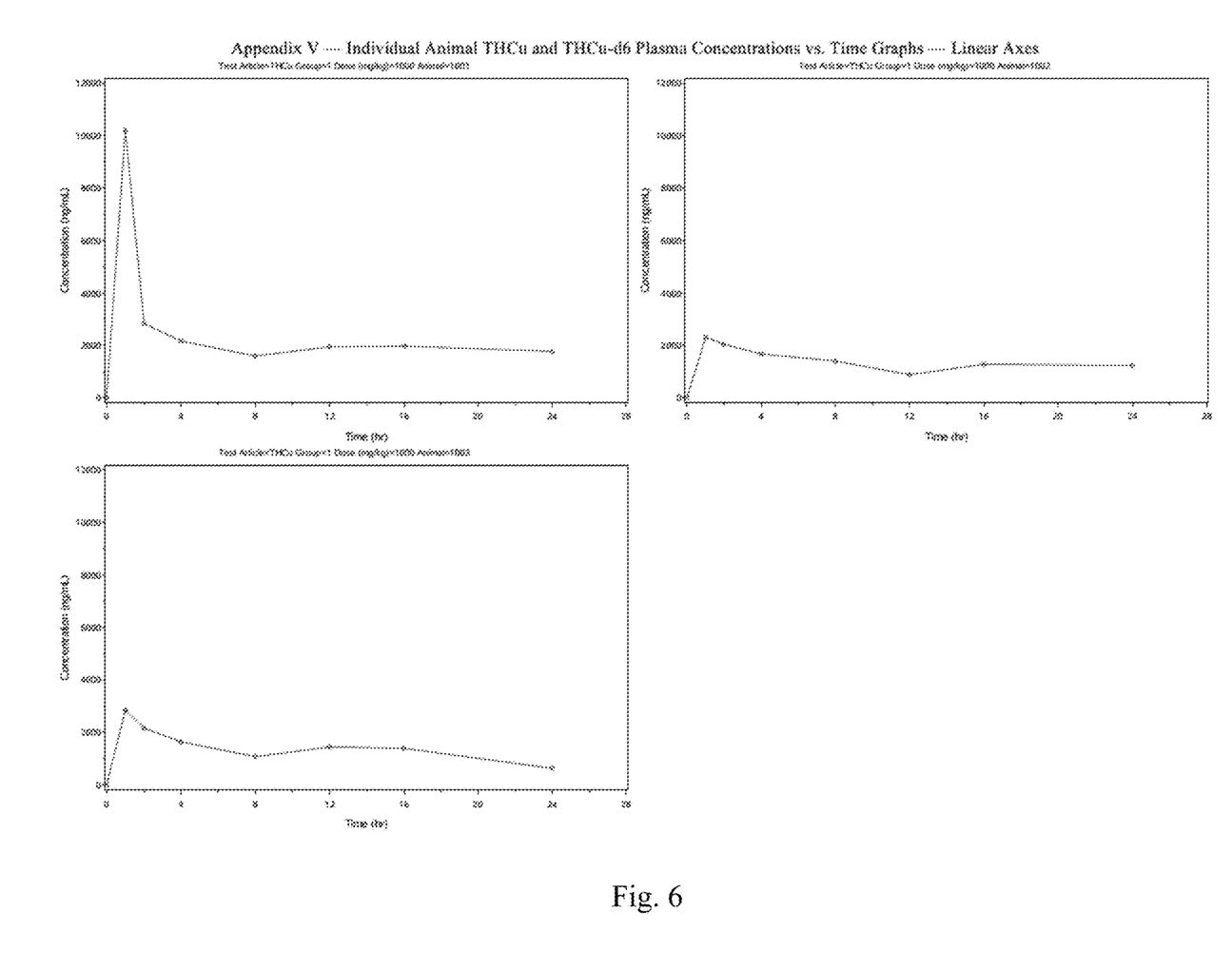
FIG. 6 shows graphs of individual animal THCu plasma concentrations versus time using linear axis.
Figure 7:
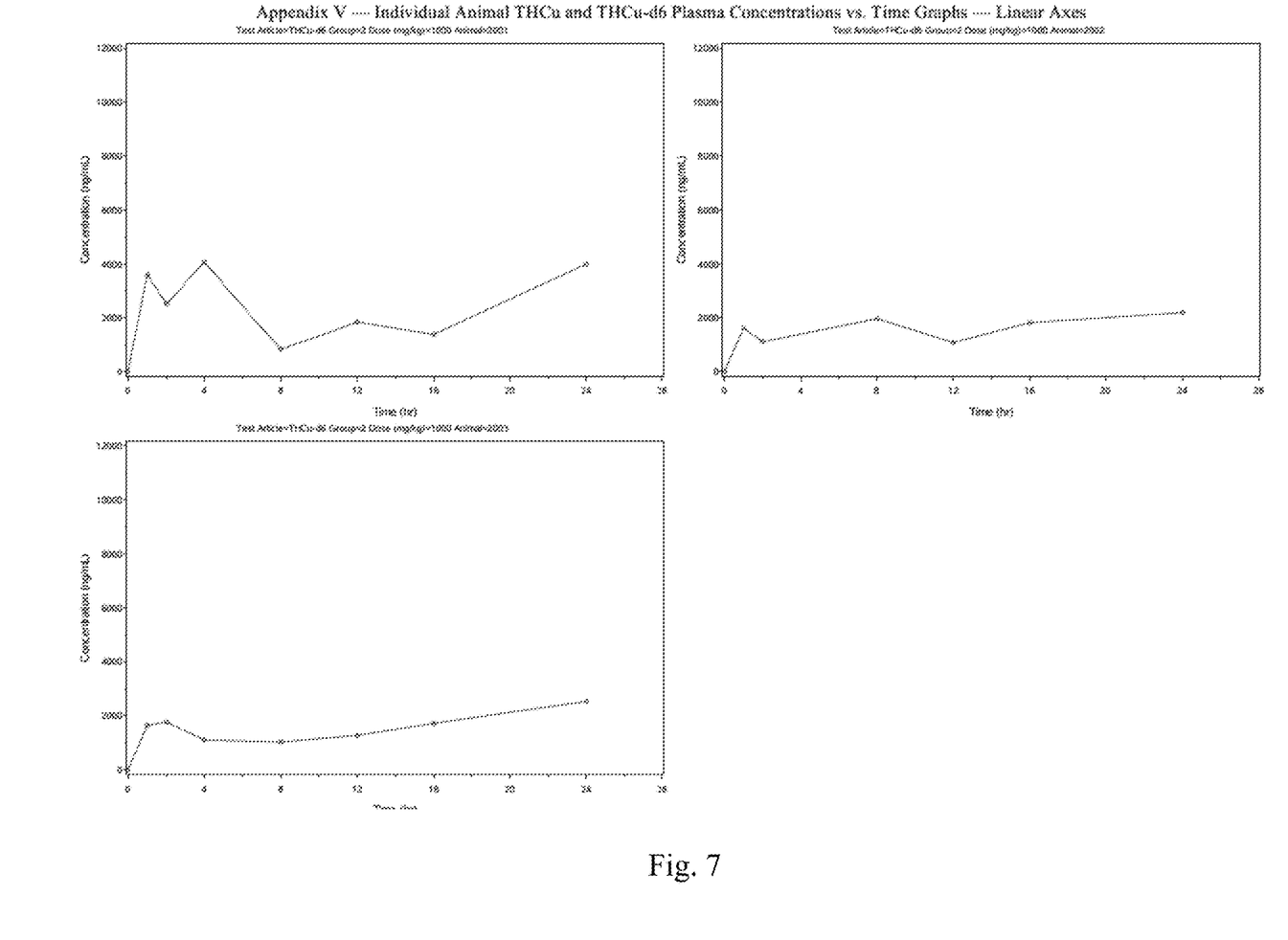
FIG. 7 shows graphs of individual animal THCu-d6 plasma concentrations versus time using linear axis.
Figure 8:
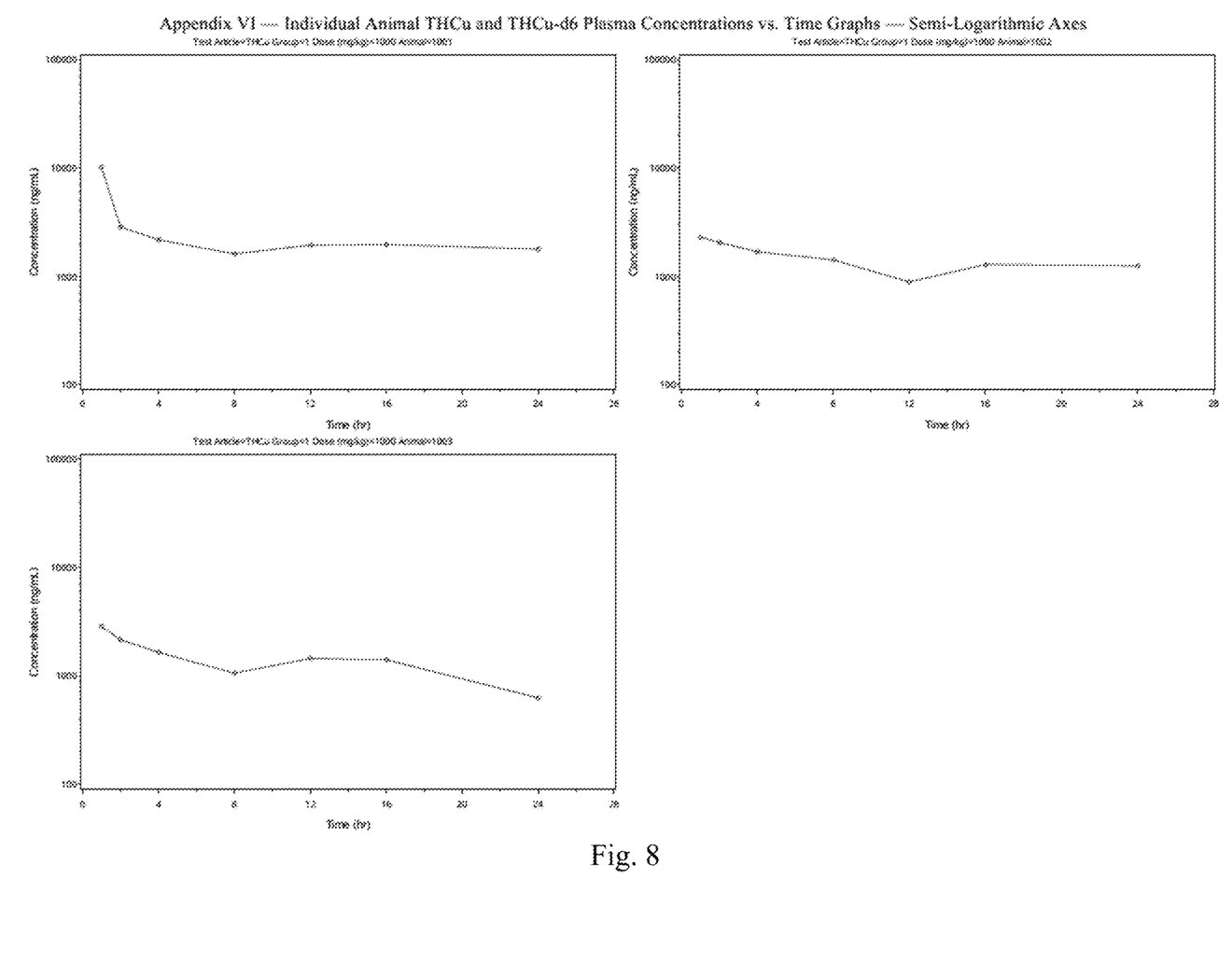
FIG. 8 shows graphs of individual animal THCu plasma concentrations versus time using semi-logarithmic axis.
Figure 9:
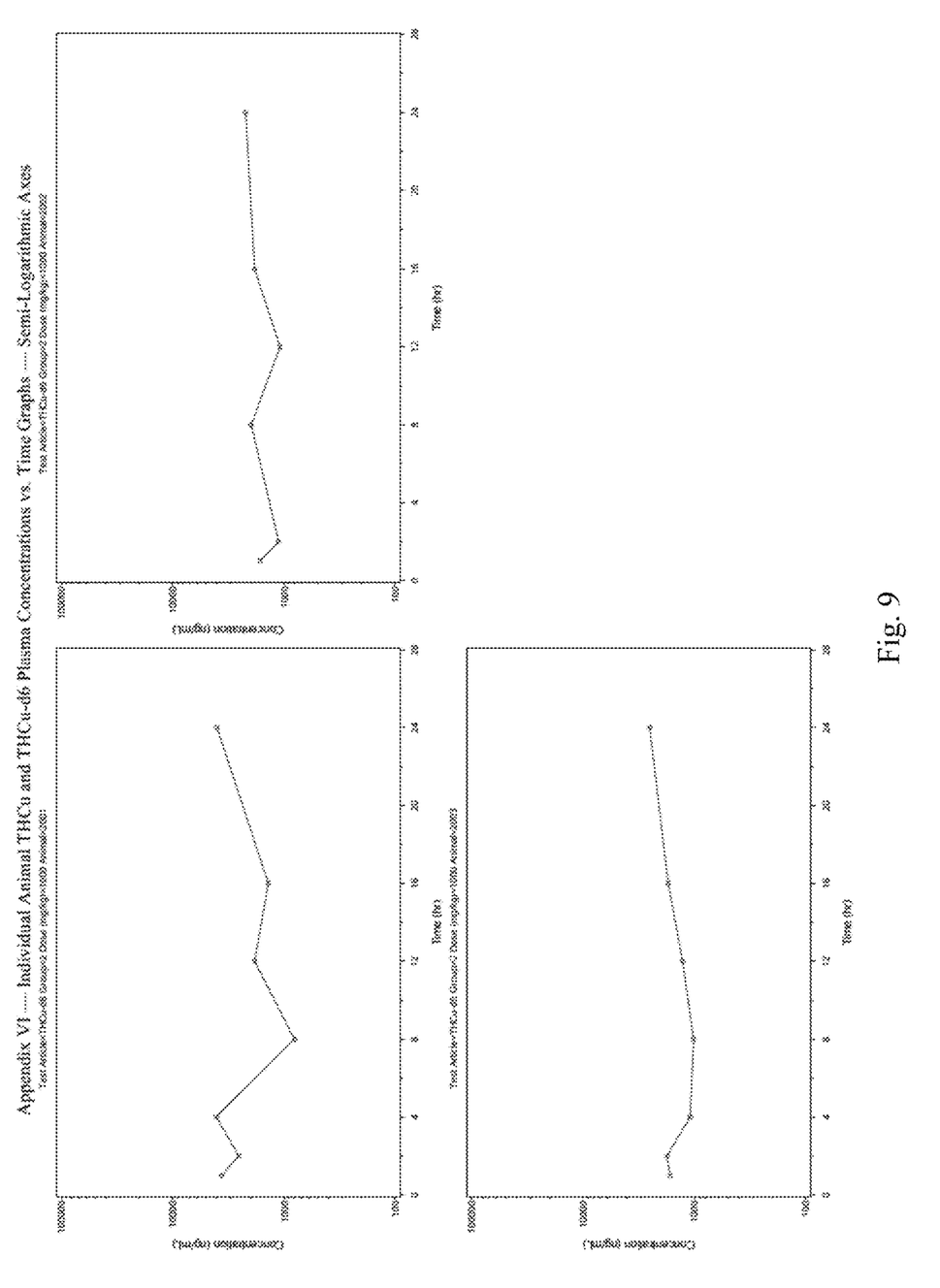
FIG. 9 shows graphs of individual animal THCu-d6 plasma concentrations versus time using semi-logarithmic axis.

Graphs of individual animal plasma concentrations versus time are shown in FIGS. 6-7 (linear axes) and FIGS. 8-9 (semi-logarithmic axes). The data show the stable plasma concentration for THCu-d6 with no burst release of active agent after administration.

Example 6

In one aspect, the invention involves a liquid THCu composition. The THCu active of this composition may be deuterated, or non-deuterated. In one example, THCu was combined with PEG 300 (25 mg/ml). THCu was combined with a PEG solubilizing agent, resulting in a liquid form of THCu. The solubilizing agent was PEG 300 at a concentration of 25 mg/ml.

The liquid composition was added to HK-2 cells in three dosages. After 3 h, HO-1 mRNA was measured. The PEG without THCu served as a control. The liquid composition exhibited a dose-dependent increase from 0.76 baseline to 1.8 at 10 μg/ml. The data demonstrate that the THCu composition described herein activates the Nrf2 pathway.

| THCu + PEG 300 (0.4%) | | | | |
| --- | --- | --- | --- | --- |
| THCu (μg/ml) | Control | 0.1 | 1 | 10 |
| Human HO-1/GAPDH mRNA | 0.76 | 0.75 | 0.87 | 1.80 |

SnPP-induced HO-1 activation on the same cell culture plate.

| Control | SnPP 10 μg/ml | SnPP 10 μg/ml |
| --- | --- | --- |
| 0.93 | 1.41 | 3.57 |

The data demonstrate that the liquid THCu compositions described above would be suitable for an injectable composition. This composition has particular advantages for acutely ill patients for whom oral administration of THCu is inconvenient or impossible. For example, the liquid THCu composition may be particularly useful for treating acute myocardial infarction, stroke, and traumatic brain injury. In one aspect, the liquid composition may be administered via the parenteral route for one or more of these indications. Alternatively, the liquid composition may be administered subcutaneously or intravenously.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A pharmaceutical composition comprising:
   a) tetrahydrocurcumin (THCu) according to the formula:

and
   b) a pharmaceutically acceptable excipient, wherein the pharmaceutical formulation lacks detectable amounts of hexahydrocurcumin (HHC) as indicated by no peak with a relative retention time of 7.14-7.15 while exhibiting a peak associated with THCu at 9.07 for THCu as determined by gas chromatography (GC).

2. The pharmaceutical composition of claim 1, wherein the pharmaceutical composition further comprises a peak at 8.23-8.25 RRT.

3. The pharmaceutical composition of claim 1, wherein pharmaceutical composition further comprises a peak at 2.75 RRT.

4. The pharmaceutical composition of claim 1, wherein the pharmaceutically acceptable excipient is phosphatidylcholine.

5. The pharmaceutical composition of claim 4, wherein the pharmaceutical composition further comprises an antioxidant selected from vitamin E, vitamin C or alpha lipoic acid.

6. The pharmaceutical composition claim 4, wherein the pharmaceutical composition further comprises curcumin, a terpenoid, cysteamine, pantethine, or baicalin.

7. The pharmaceutical composition of claim 4, wherein the pharmaceutical composition further comprises a lipophilic solvent.

8. The pharmaceutical composition of claim 4, wherein the pharmaceutical composition further comprises a sugar or cellulose preparation.

9. The pharmaceutical composition of claim 8, wherein the sugar is lactose, sucrose, mannitol, or sorbitol.

10. The pharmaceutical composition of claim 8, wherein the cellulose preparation is
maize starch, wheat starch, rice starch, potato starch, gelatin, gum tragacanth, methyl cellulose, hydroxypropylmethylcellulose, sodium carboxymethylcellulose, or polyvinylpyrrolidone (PVP).

11. The pharmaceutical composition of claim 1, wherein the pharmaceutically acceptable excipient is polyenylphosphatidylcholine.

12. The pharmaceutical composition of claim 11, wherein the pharmaceutical composition comprises at least 5% of the polyenylphosphatidylcholine by weight and no more than 95% of the polyenylphosphatidylcholine by weight.

13. The pharmaceutical composition of claim 1, wherein pharmaceutical composition comprises 10% THCu by weight.

14. The pharmaceutical composition of claim 1, wherein the THCu is deuterated.

15. The pharmaceutical composition of claim 13, wherein the THCu is THCu-d6.

16. The pharmaceutical composition of claim 4, wherein the pharmaceutical composition further comprises a fatty oil.

17. The pharmaceutical composition of claim 4, wherein the pharmaceutical composition further comprises an organic oil.

* * * * *